United States Patent
Amborn et al.

(10) Patent No.: US 10,737,087 B2
(45) Date of Patent: Aug. 11, 2020

(54) FILLING FITTING

(71) Applicant: Smiths Medical ASD, Inc., Rockland, MA (US)

(72) Inventors: Chad Amborn, Minneapolis, MN (US); Geoff Clark, Lempster, NH (US); Renee Robert, Shoreview, MN (US)

(73) Assignee: SMITHS MEDICAL ASD, INC., Plymouth, MN (US)

( * ) Notice: Subject to any disclaimer, the term of this patent is extended or adjusted under 35 U.S.C. 154(b) by 1302 days.

(21) Appl. No.: 13/860,770

(22) Filed: Apr. 11, 2013

(65) Prior Publication Data

US 2013/0270819 A1 Oct. 17, 2013

Related U.S. Application Data

(60) Provisional application No. 61/625,300, filed on Apr. 17, 2012.

(51) Int. Cl.
*A61M 39/10* (2006.01)
*A61M 5/31* (2006.01)
*A61M 39/18* (2006.01)

(52) U.S. Cl.
CPC ............ *A61M 39/10* (2013.01); *A61M 39/18* (2013.01); *A61M 2005/3114* (2013.01);
(Continued)

(58) Field of Classification Search
CPC ................ A61M 39/10; A61M 39/18; A61M 2005/3114; A61M 2039/1094; F16L 2201/60; Y10T 29/49428
(Continued)

(56) References Cited

U.S. PATENT DOCUMENTS 1,871,370 A    8/1932   Jacques
2,564,804 A *   8/1951   Everett .......................... 285/38
(Continued)

FOREIGN PATENT DOCUMENTS

EP    217055    4/1987
EP    774270    5/1997
(Continued)

OTHER PUBLICATIONS

Chinese Office Action dated Apr. 6, 2012 re: CN Appln No. 2011101192607.
(Continued)

*Primary Examiner* — Zachary T Dragicevich
(74) *Attorney, Agent, or Firm* — Louis Woo (57) ABSTRACT

A fitting has a first end conventional connector and a second end non-conventional connector of a given configuration that is matable only to a counterpart non-conventional connector having a configuration complementary to the given configuration. The body of the fitting has two extending wings that merge with a partition that separates the conventional connector from the body. A label may be mounted about the neck extension of the male connector to convey information to the user. The portion along the fitting between the label and the partition provides a location whereat the user can position his fingers to grasp the fitting. The partition prevents the fingers of the user from coming into contact with and contaminating the conventional connector, while the label, in addition to conveying information to the user, also acts a barrier to prevent contamination of the non-conventional connector by the fingers of the user.

20 Claims, 6 Drawing Sheets

(52) U.S. Cl.
CPC . *A61M 2039/1094* (2013.01); *A61M 2207/00* (2013.01); *F16L 2201/60* (2013.01); *Y10T 29/49428* (2015.01)

(58) Field of Classification Search
USPC .............................................. 285/332, 332.1
See application file for complete search history.

(56) References Cited

U.S. PATENT DOCUMENTS

| | | | |
|---|---|---|---|
| 3,170,667 A | 2/1965 | Szohatzky | |
| 3,287,031 A | 11/1966 | Simmons et al. | |
| 4,006,744 A | 2/1977 | Steer | |
| 4,076,285 A | 2/1978 | Martinez | |
| 4,080,737 A | 3/1978 | Fleer | |
| 4,116,476 A | 9/1978 | Porter et al. | |
| 4,137,917 A | 2/1979 | Cohen | |
| 4,150,673 A | 4/1979 | Watt | |
| 4,211,439 A | 7/1980 | Moldestad | |
| 4,294,250 A * | 10/1981 | Dennehey | 604/403 |
| 4,452,473 A | 6/1984 | Ruschke | |
| 4,453,927 A | 6/1984 | Sinko | |
| 4,619,640 A | 10/1986 | Potoisky | |
| 4,682,981 A | 7/1987 | Suzuki et al. | |
| 4,723,948 A | 2/1988 | Clark et al. | |
| 4,758,225 A | 7/1988 | Cox et al. | |
| 4,790,567 A | 12/1988 | Kawano et al. | |
| 4,940,458 A | 7/1990 | Cohn | |
| 4,950,255 A | 8/1990 | Brown et al. | |
| 5,053,015 A | 10/1991 | Gross et al. | |
| 5,069,225 A | 12/1991 | Okamura | |
| 5,078,703 A | 1/1992 | Bryant | |
| 5,127,626 A | 7/1992 | Hilal et al. | |
| 5,211,637 A | 5/1993 | Goto et al. | |
| 5,280,723 A | 1/1994 | Aharoni et al. | |
| 5,312,337 A | 5/1994 | Flaherty et al. | |
| 5,348,048 A * | 9/1994 | Schirado et al. | 137/588 |
| 5,393,101 A | 2/1995 | Matkovich | |
| 5,405,339 A | 4/1995 | Kohnen et al. | |
| 5,405,340 A | 4/1995 | Fageol et al. | |
| 5,538,399 A | 7/1996 | Johnson | |
| 5,545,152 A | 8/1996 | Funderburk et al. | |
| 5,562,121 A | 10/1996 | Hodges et al. | |
| 5,591,143 A | 1/1997 | Trombley, III et al. | |
| D378,130 S | 2/1997 | Schmidt | |
| 5,605,359 A | 2/1997 | Hoff | |
| D378,405 S | 3/1997 | Musgrave et al. | |
| 5,616,133 A | 4/1997 | Cardenas | |
| 5,620,427 A | 4/1997 | Werschmidt et al. | |
| 5,632,735 A | 5/1997 | Wyatt et al. | |
| 5,651,776 A | 7/1997 | Appling et al. | |
| 5,688,254 A | 11/1997 | Lopez et al. | |
| 5,695,473 A | 12/1997 | Olsen | |
| 5,702,371 A | 12/1997 | Bierman | |
| 5,725,511 A | 3/1998 | Urrutia | |
| 5,741,084 A | 4/1998 | Del Rio et al. | |
| 5,741,269 A | 4/1998 | McCredy | |
| 5,749,861 A | 5/1998 | Guala et al. | |
| 5,810,398 A | 9/1998 | Matkovich | |
| 5,853,391 A | 12/1998 | Bell | |
| 5,855,230 A | 1/1999 | Guala et al. | |
| 5,925,028 A | 7/1999 | Delvigo | |
| 5,947,937 A | 9/1999 | Urrutia et al. | |
| D417,733 S | 12/1999 | Howell et al. | |
| D421,119 S | 2/2000 | Musgrave et al. | |
| 6,027,480 A | 2/2000 | Davis et al. | |
| 6,099,519 A | 8/2000 | Olsen et al. | |
| 6,156,025 A | 12/2000 | Niedospial et al. | |
| 6,171,281 B1 | 1/2001 | Zhang | |
| 6,197,007 B1 | 3/2001 | Thorne et al. | |
| 6,217,564 B1 | 4/2001 | Peters et al. | |
| 6,244,632 B1 | 6/2001 | Gasparini | |
| 6,309,543 B1 | 10/2001 | Fenton | |
| D452,003 S | 12/2001 | Niermann | |
| D452,314 S | 12/2001 | Niermann | |
| 6,350,260 B1 | 2/2002 | Goebel et al. | |
| 6,402,207 B1 * | 6/2002 | Segal | A61M 39/10 285/330 |
| D459,870 S | 7/2002 | St. Louis | |
| 6,422,607 B1 | 7/2002 | Kirby | |
| 6,428,514 B1 | 8/2002 | Goebel et al. | |
| 6,475,190 B2 | 11/2002 | Young | |
| 6,500,153 B1 | 12/2002 | Sheppard et al. | |
| 6,506,181 B2 | 1/2003 | Meng et al. | |
| 6,511,472 B1 | 1/2003 | Hayman et al. | |
| 6,524,304 B1 | 2/2003 | Picou et al. | |
| 6,524,589 B1 | 2/2003 | Reichert et al. | |
| 6,536,805 B2 | 3/2003 | Matkovich | |
| 6,558,353 B2 | 5/2003 | Zohmann | |
| 6,612,624 B1 | 9/2003 | Segal et al. | |
| 6,656,161 B2 | 12/2003 | Young et al. | |
| 6,676,652 B2 | 1/2004 | Mogg | |
| 6,688,651 B2 | 2/2004 | Min-cheol | |
| 6,722,705 B2 | 4/2004 | Korkor | |
| 6,786,131 B2 | 9/2004 | Tsai | |
| 6,802,836 B2 | 10/2004 | Bouphavichith et al. | |
| 6,843,513 B2 | 1/2005 | Guala | |
| 6,893,056 B2 | 5/2005 | Guala | |
| 6,953,448 B2 | 10/2005 | Moulton et al. | |
| 6,988,423 B2 | 1/2006 | Bolam et al. | |
| 7,044,936 B2 | 5/2006 | Harding | |
| 7,115,228 B2 | 10/2006 | Lundtveit et al. | |
| 7,240,927 B2 | 7/2007 | Chang | |
| 7,270,349 B2 | 9/2007 | Bamberger et al. | |
| 7,344,527 B2 | 3/2008 | Schweikert et al. | |
| 7,481,796 B2 | 1/2009 | Nishtala et al. | |
| 7,571,889 B2 | 8/2009 | Miyahara | |
| 7,635,354 B2 | 12/2009 | Navarro | |
| 7,641,648 B2 | 1/2010 | Bouphavichitch et al. | |
| 7,857,805 B2 | 12/2010 | Raines | |
| 7,955,315 B2 | 6/2011 | Feinberg et al. | |
| 2001/0049490 A1 | 12/2001 | Slanda et al. | |
| 2002/0079258 A1 | 6/2002 | Sawa | |
| 2002/0151838 A1 | 10/2002 | Beck et al. | |
| 2003/0105428 A1 | 6/2003 | Hogan et al. | |
| 2004/0162544 A1 | 8/2004 | Raulerson et al. | |
| 2004/0167474 A1 | 8/2004 | Meng et al. | |
| 2004/0201216 A1 | 10/2004 | Segal et al. | |
| 2005/0090801 A1 | 4/2005 | Racz et al. | |
| 2005/0146136 A1 * | 7/2005 | Kawamura | A61M 39/10 285/255 |
| 2005/0209581 A1 | 9/2005 | Butts et al. | |
| 2005/0225082 A1 | 10/2005 | Dalle et al. | |
| 2006/0015086 A1 | 1/2006 | Rasmussen et al. | |
| 2006/0271000 A1 | 11/2006 | Randelletta et al. | |
| 2007/0060898 A1 * | 3/2007 | Shaughnessy et al. | 604/284 |
| 2007/0088329 A1 | 4/2007 | Bierman | |
| 2007/0225683 A1 | 9/2007 | Raulerson et al. | |
| 2007/0270758 A1 | 11/2007 | Hanner et al. | |
| 2008/0065023 A1 * | 3/2008 | Kennard | 604/187 |
| 2008/0177250 A1 | 7/2008 | Howlett et al. | |
| 2008/0183154 A1 | 7/2008 | Racz et al. | |
| 2008/0287919 A1 | 11/2008 | Kimball | |
| 2008/0294146 A1 | 11/2008 | Charlez | |
| 2008/0312640 A1 | 12/2008 | Grant | |
| 2009/0187165 A1 | 7/2009 | Kaern | |
| 2009/0187166 A1 | 7/2009 | Young | |
| 2009/0204105 A1 | 7/2009 | Johansson et al. | |
| 2009/0243281 A1 | 10/2009 | Seifert et al. | |
| 2009/0270842 A1 | 10/2009 | Blocher et al. | |
| 2009/0292273 A1 | 11/2009 | Racz et al. | |
| 2009/0299339 A1 | 12/2009 | Young | |
| 2010/0022951 A1 | 1/2010 | Ferrera et al. | |
| 2010/0094260 A1 | 4/2010 | Cude et al. | |
| 2011/0137294 A1 * | 6/2011 | Calimeri et al. | 604/533 |
| 2011/0230856 A1 * | 9/2011 | Kyle et al. | 604/416 |
| 2012/0123392 A1 * | 5/2012 | McKinnon et al. | 604/533 |

FOREIGN PATENT DOCUMENTS

| | | |
|---|---|---|
| EP | 1010439 | 6/2000 |
| FR | 2642139 | 7/1990 |
| GB | 771967 | 4/1957 |
| JP | 2001-187990 | 7/2001 |

(56) References Cited

FOREIGN PATENT DOCUMENTS

| WO | 1997/032618 | 9/1997 |
| WO | 2005/044335 | 10/2004 |
| WO | 2006/125789 | 11/2006 |

OTHER PUBLICATIONS

Canadian Office Action dated Apr. 13, 2012 re: CA Appln No. 2575136.
Sheppard et al., "Improving patient safety by design—a new spinal/intrathecal injection safety system", Can J Anesth 2006; 0108-9.

\* cited by examiner

FILLING FITTING

CROSS REFERENCE TO RELATED APPLICATION

This application claims priority from provisional application No. 61/625,300 filed Apr. 17, 2012.

FIELD OF THE INVENTION

The present invention relates to connector fittings and more particularly to a filling fitting adapted to be used with medicament infusion systems, for example those disclosed in co-pending applications entitled "Medicament Infusion Systems" (application No. 61/457,879 filed Jun. 27, 2011) and "Fitting For Medicament Infusion Systems" (application No. 61/573,094 filed Aug. 31, 2011). The respective disclosures of the 61/457,879 and 61/573,094 applications are incorporated by reference herein.

BACKGROUND OF THE INVENTION

In the aforenoted "Medicament Infusion Systems", fluid medicament is infused into the patient from a fluid storage cassette. The instant invention fitting provides the means by which the cassette may be filled with the medicament.

SUMMARY OF THE PRESENT INVENTION

The filling fitting of the instant invention is adapted to be used by a pharmacist or the appropriate medical personnel to fill or refill the fluid store of a cassette to be used with a medicament infusion system. The inventive filling fitting prevents mis-connection among connectors to ensure that the correct medicament is input to the cassette.

The inventive filling fitting has a substantially cylindrical longitudinal body that includes a first end having a conventional female luer connector and a second end having a non-conventional male connector with a given configuration that allows it to only mate with a counterpart non-conventional female connector having a configuration complementary to the given configuration. The non-conventional connectors are disclosed in the 61/457,879 application and may be referred to as CorrectInject® (CI) connectors. Extending along a substantial portion of the main portion of the body in opposite directions towards the female luer end are two wings that merge with a partition extending circumferentially about the body away from the first end. The female luer connector at the first end is thus separated from the main body portion of the fitting by the partition. The partition prevents the female luer connector from being inadvertently touched and contaminated by the fingers of the user.

The non-conventional male connector may be fittingly attached to an opening at the other end of the body of the fitting and bonded thereto by any number of conventional methods and means such as by ultrasonic welding or solvent. Before being attached to the opening of the fitting, a substantially planar member that may be a Tyvek sheet or card is fittedly mounted about the neck extension of the non-conventional male connector, so that once the neck extension is slidably inserted to the opening of the body of the fitting, the Tyvek member is not removable from and becomes a part of the fitting. Indicia may be provided on the tyvek sheet, by printing for example, to convey information to the user. Similar to the partition that shields the female luer end, the planar member prevents the fingers of the user from inadvertently coming into contact with the non-conventional male connector. The planar member and the partition provide two points of demarcation along the body of the fitting that define a general location along the body of the fitting whereat the fingers of the user may be positioned to grasp the fitting. The oppositely extending wings provide a finger mechanism for the user to grasp and rotate the fitting.

The conventional female luer connector of the fitting is matable to a conventional male luer connector of a medicament store such as a syringe or other types of fluid container, whereas the non-conventional male connector of the fitting is matable to a counterpart non-conventional female connector that forms the input of the medicament store or cassette. As a result, the filling fitting of the instant invention is adapted to interposedly connect a fluid source with a conventional luer to its first end and a fluid store with a specially designed non-conventional connector to its second end to establish a fluid path between the fluid source and the fluid store.

Instead of being directly connected to each other, the non-conventional male connector and the main body portion of the fitting may be connected by a tubing where one of the ends of the tubing is fixedly attached to the male connector while the other of its ends is fixedly connected to the opening at the main body portion of the fitting. The tubing therefore provides for a fitting having a built in extension tubing that provides flexibility for the fitting.

The fitting of the instant invention therefore comprises a body including a main portion, a first end and a second end, and a through passage in the body connecting the first and second ends. The first end has a conventional connector. The second end has a non-conventional connector with a given configuration that prevents it from mating with a counterpart conventional connector but allows it to mate with a counterpart non-conventional connector having a configuration complementary to the given configuration. The fitting further comprises at least one wing extending from and longitudinally along at least a part of the main portion of the body and a partition that extends circumferentially about the body. The end of the wing facing the first end merges with the partition. The partition separates the first end from the main portion of the body to thereby prevent the fingers of a user from inadvertently coming into contact with the first end of the fitting.

The present invention is also directed to a method of manufacturing a fitting adapted to establish a fluid path between a fluid store and a fluid source, comprising the steps of:
(a) providing a body that includes a main portion, a first end and a second end, and a through passage in the body connecting the first and second ends;
(b) providing a conventional connector at the first end;
(c) providing a non-conventional connector at the second end, the non-conventional connector having a given configuration that prevents it from mating with a counterpart conventional connector but matable with a counterpart connector having a configuration complementary to the given configuration;
(d) extending at least one wing from and longitudinally along at least a part of the main portion of the body; and
(e) extending a partition circumferentially about the body, the end of the wing facing the first end merging with the partition, the partition separating the first end from the main portion of the body.

BRIEF DESCRIPTION OF THE FIGURES

The present invention will become apparent and the invention itself will be best understood by reference to the following description of the present invention taken in conjunction with the accompanying drawings wherein.

DETAILED DESCRIPTION OF THE INVENTION

Figure 1:
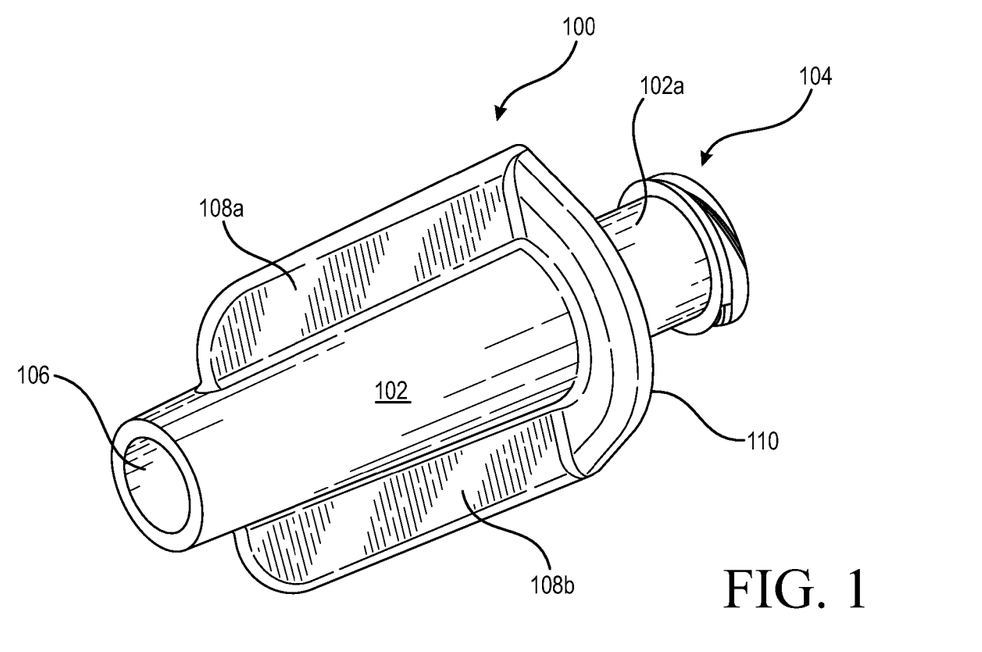
FIG. 1 is a perspective view of the filling fitting of the instant invention sans its non-conventional connector.
Figure 2:
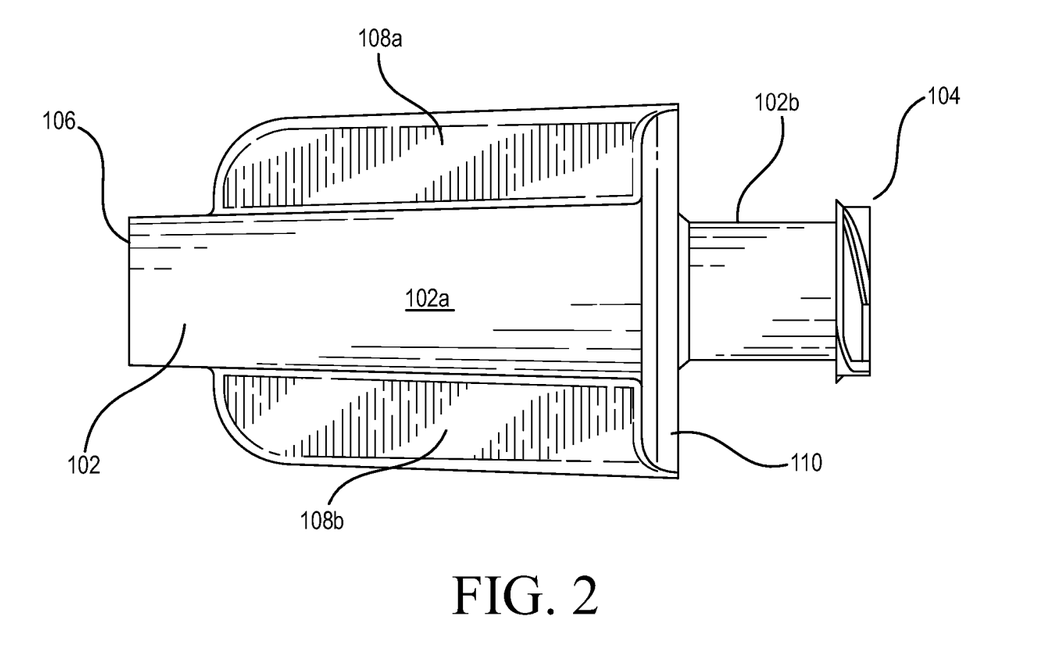
FIG. 2 is a side view of the fitting of FIG. 1.
Figure 3:
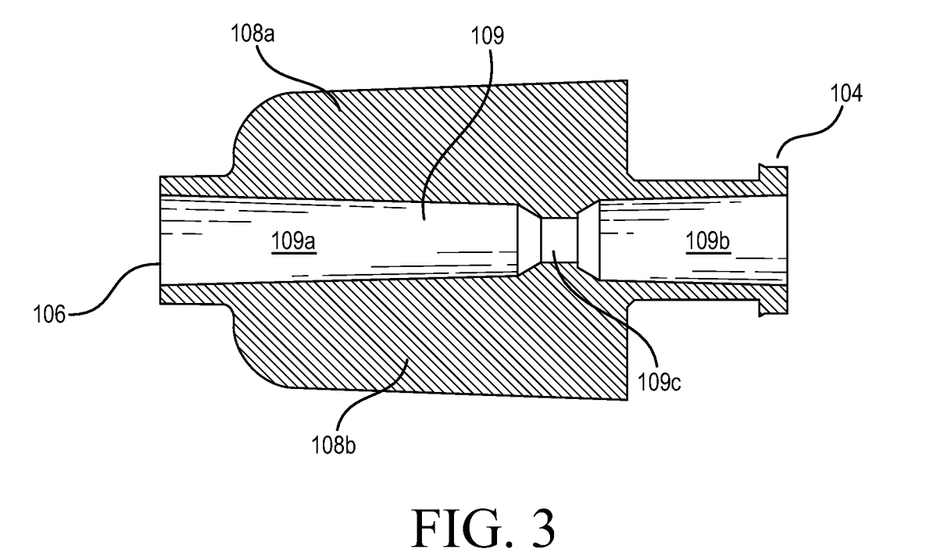
FIG. 3 is a cross-sectional view of the fitting of FIG. 1.

With reference to FIGS. 1-3, the filling fitting 100 of the instant invention is shown to have a longitudinal cylindrical body 102 having a main portion 102a. At a first or one end of the fitting there is formed a conventional female luer connector, or simply female luer 104. As disclosed in the aforenoted incorporated by reference application 61/457,879 (now Ser. No. 13/517,782), standard or conventional luer connectors are manufactured in accordance with the current ISO (International Standard Organization) Standards 594-1 and 594-2. The second or other end of the fitting 100 has, for the embodiment shown in FIGS. 1-3, an opening 106 wherein a neck extension of a non-conventional connector is slidably fitted, as will be described infra. As shown, two wings 108a and 108b extend in opposite directions substantially along main portion 102a of body 102. Wings 108a and 108b may or may not extend along the entire length of main portion 102a. A partition 110 extends circumferentially proximate to female luer 104 of the fitting and has a surface away from the female luer end that merges with the respective ends of wings 108a and 108b that face the female luer end of the fitting. Partition 110 prevents the fingers of the user from inadvertently touching and thereby contaminating the female luer end of the fitting. As shown in FIGS. 1-3, a portion 102b of body 102 separates female luer 104 from partition 110.

FIG. 3 is a cross-sectional view of the fitting showing a through passage 109 that connects the first end of the body of the fitting, represented by female luer 104, to the second end of the fitting, represented by opening 106. The through passage 109 has a first passage 109a joined to a second passage 109b by a neck passage 109c. the configuration of the neck passage 109c results from the manufacturing process used to form passages 109a and 109b.

Figure 4:
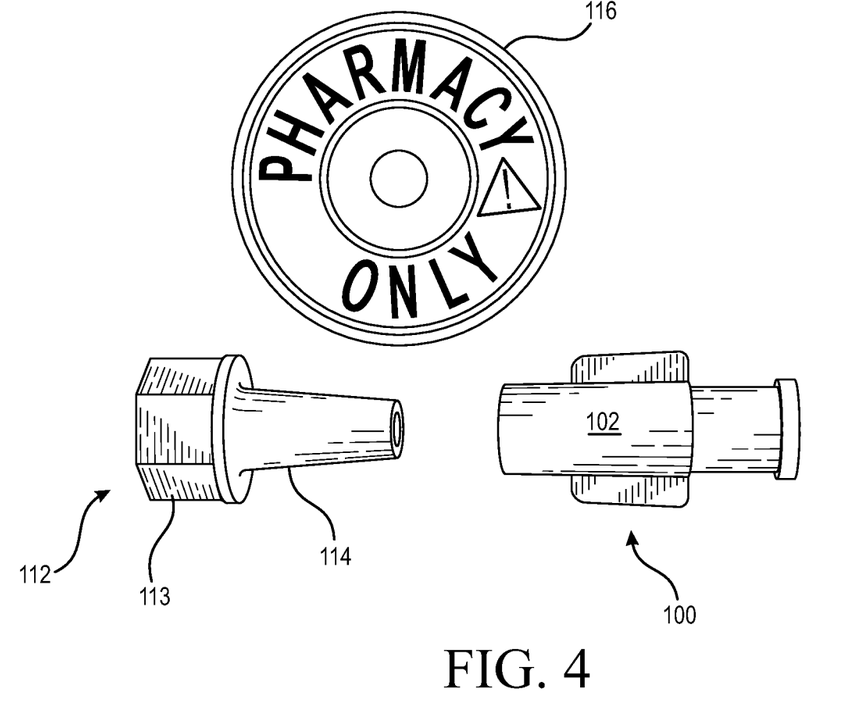
FIG. 4 is an illustration of the non-conventional connector and the information conveying component of the fitting of the instant invention, as well as an earlier version of a fitting body that does not have the partition shown in FIG. 1.

The non-conventional male connector, as a standalone component 112, is shown in FIG. 4. The particulars of the non-conventional male connector, which may be referred to as a male CorrectInject® (CI) connector as noted above, is described in greater detail in the aforenoted 61/457,879 (now Ser. No. 13/517,782) application, where non-conventional connectors are defined to be designed such that they are incompatible with the luer connectors that are manufactured in accordance with the current ISO (International Standard Organization) Standards 594-1 and 594-2. As shown, non-conventional male connector 112 has a connector end represented by male CI connector 113 and a neck extension 114. Neck extension 114 is slidably fitted to opening 106 of fitting 100 and is frictionally bonded thereto by conventional means and/or processes such as solvent and ultrasonic welding so that connector 112 is non-removable from the body 102 of the fitting once it is fixedly attached thereto.

Figure 5:
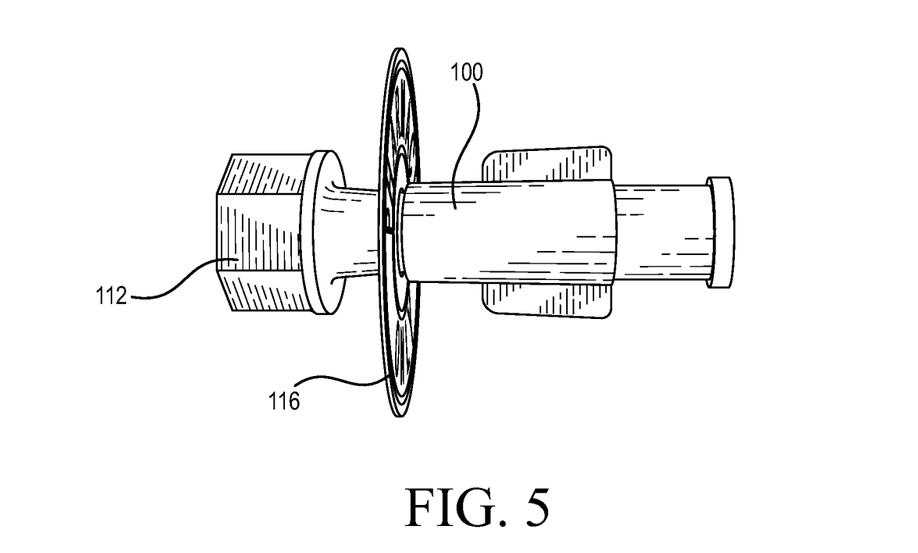
FIG. 5 is an assembled fitting that does not have the partition.

Prior to being coupled to the main portion 102a, a substantially planar and possibly circular member 116 with a center opening that may be made from Tyvek is mounted about neck extension 114 so that, when connector 112 is fitted to the main portion 102a of the fitting, member 116 becomes a barrier between the main portion 102b and the non-conventional male connecter 113, per shown in FIG. 5. Note that the main portion 102a shown in FIGS. 4 and 5 is a representation of an earlier version of the inventive fitting that does not have the partition 110 shown in FIGS. 1-3.

Figure 6:
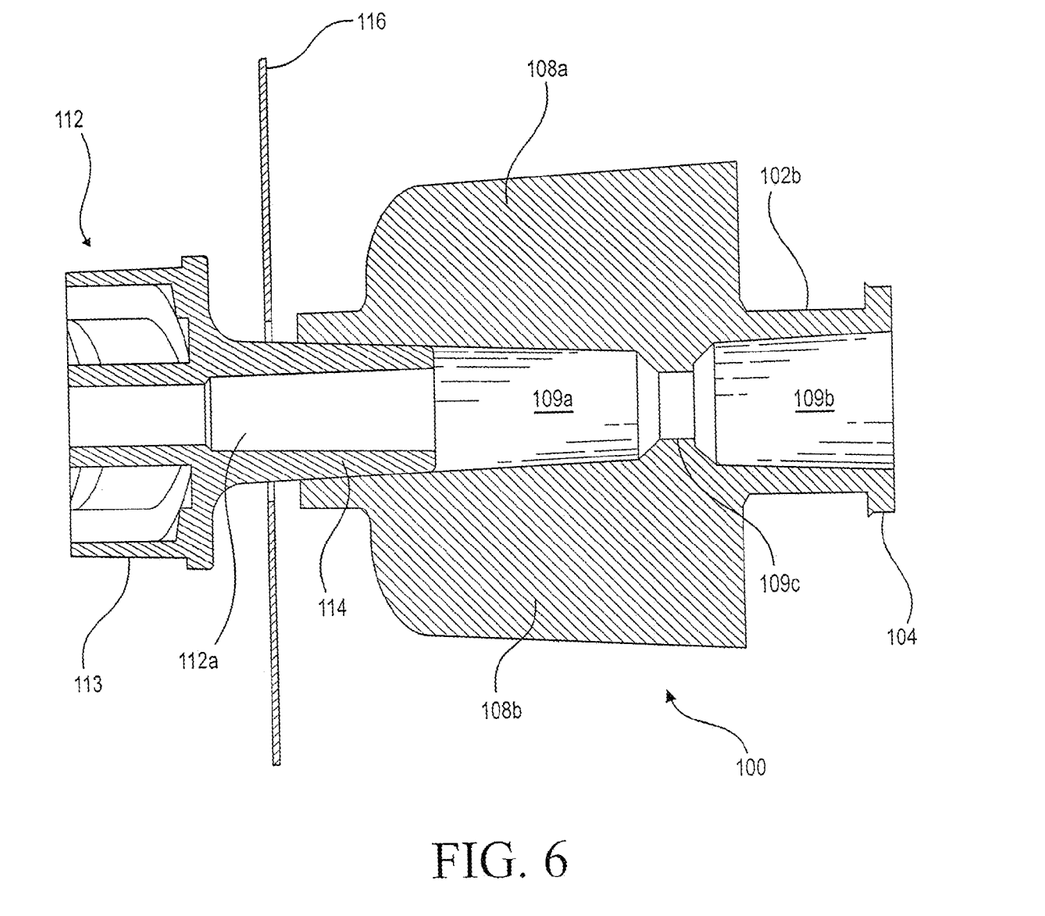
FIG. 6 is a cross-section view of the fitting of the instant invention showing the non-conventional connector bondedly attached to the open end of the main body of the fitting.

FIG. 6 is a cross-sectional view of the fitting 100 of the instant invention showing the non-conventional male connector bondedly fitted to the main body portion of the fitting. As shown, neck extension 114 of connector 112 is fittingly mated to the opening 106 along a portion of through passage 109a, and is fixedly attached thereto as discussed above, so that connector 112 is not removable from the fitting. A through passage 112a extends along connector 112, so that a through channel or passage extends from the female luer end to the non-conventional male connector end of the fitting to allow fluid to pass between the two ends.

Per shown in FIG. 6, member 116 is non-removably attached to the fitting. In addition to acting as a barrier to prevent the fingers of the user from inadvertently coming into contact with and possibly contaminating the non-conventional male connector, member 116 also acts as a label means by which indicia may be presented to the user to convey information. For example, as shown in FIG. 4, the message "Pharmacy Only" may be printed onto the Tyvek label member to inform the user that the fitting is to be used only by a pharmacist or appropriate medical personnel for filling the fluid store or cassette with a medicament from a medicament source.

When fully assembled as shown in FIG. 6, filling fitting 100 has a conventional connector in the form of a female luer 104 at its one or first end, and a non-conventional connector 112 in the form of a male CI connector at its other or second end. Thus, the first end of the fitting may be readily mated to a counterpart conventional male luer of a fluid store source such as a syringe, while the non-conventional male connector 112 is matable only to a counterpart non-conventional female connector that has a configuration complementary to the given configuration of the non-conventional male connector. In the shown exemplar embodiment, the counterpart non-conventional female (CI) connector may be an inlet for a fluid cassette whereinto medicament from a fluid source is input for filling or refilling it. Once the cassette is filled with the appropriate amount of medicament, filling fitting 110 is removed from the female CI connector, which may then be removably coupled to a counterpart non-conventional male CI connector of a tubing or medical device (such as an extension set to catheter, needle or cannula that may be inserted to a patient) for infusing the medicament to the patient. The counterpart non-conventional male connector of the tubing or medical device would have the same given configuration as the non-conventional male CI connector 112 of filling fitting 100.

Figure 7:
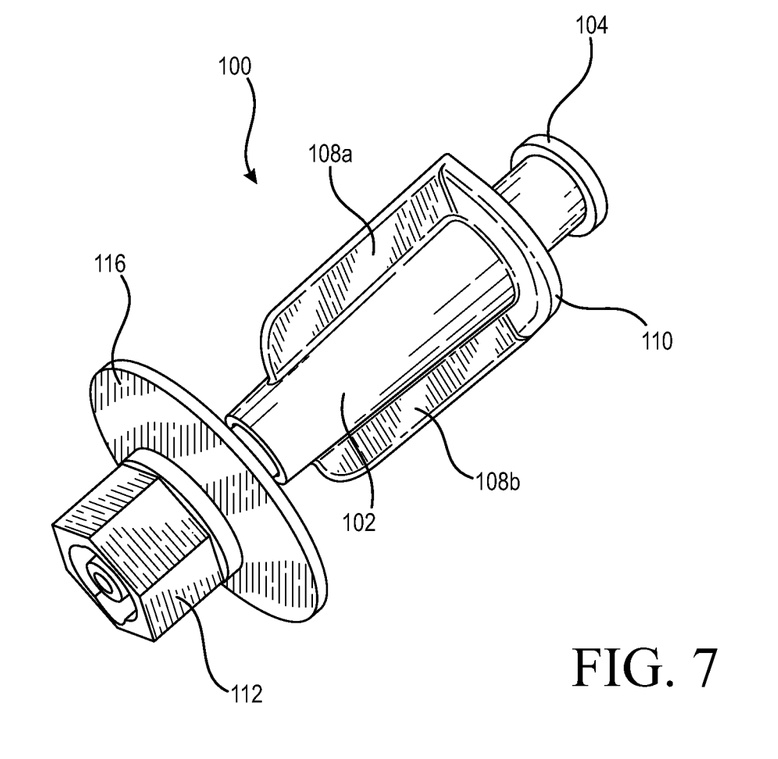
FIG. 7 is a perspective view of the filling fitting of the instant invention.

FIG. 7 is perspective view of the fitting of the instant invention.

Figure 8:
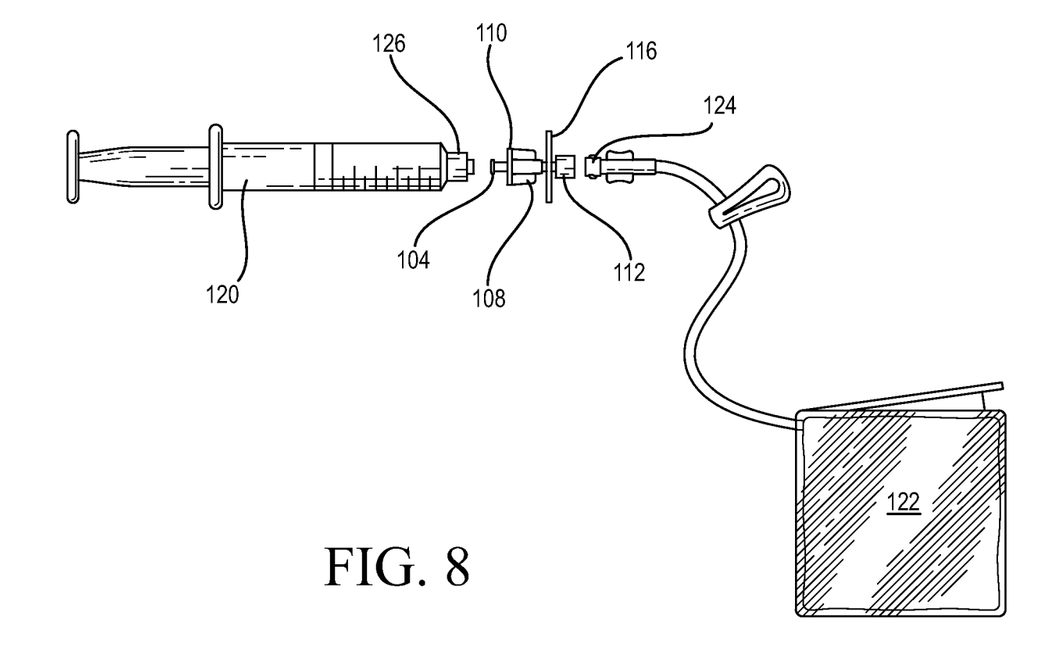
FIG. 8 shows the filling fitting of the instant invention interposed between a medication source in the form of a syringe and a fluid store cassette.

With reference to FIG. 8, the filling fitting 100 of the instant invention is shown to be interposed between a medicament source in the form of a syringe 120 and a fluid store cassette 122. Without limitations, the medicament source may also be a medication bottle, a medication bag or other types of medication container. As described in detail in the above-noted 61/457,879 application, the input connector 124 to the cassette is a non-conventional CI female connector that has a configuration complementary to the given configuration of the non-conventional male CI connector 112 of fitting 100. Accordingly, CI connectors 112 and 124 are readily matable to each other. The output connector 126 for the syringe 120, on the other hand, is a conventional male luer connector that is matable to the conventional female luer connector 104 of fitting 100. With both sets of matching connectors matingly coupled, a fluid path is established between syringe 120 and cassette 122 to thereby enable the pharmacist to fill the cassette with the fluid medicament from syringe 120. Once the cassette is filled with the desired amount of medicament or medication, the filling fitting is removed from the input connector of the cassette. The cassette may then be fluidly connected to a pump or other devices so that the medicament stored therein may be infused to a patient.

Although shown as a separate component that is fixedly attached to the body of the fitting in FIGS. 4 and 5, non-conventional male connector 112 may in practice be formed as an integral part of the filling fitting so that the filling fitting is a one piece integral adapter fitting with a conventional connector at one end and a non-conventional connector at its other end.

Figure 9:
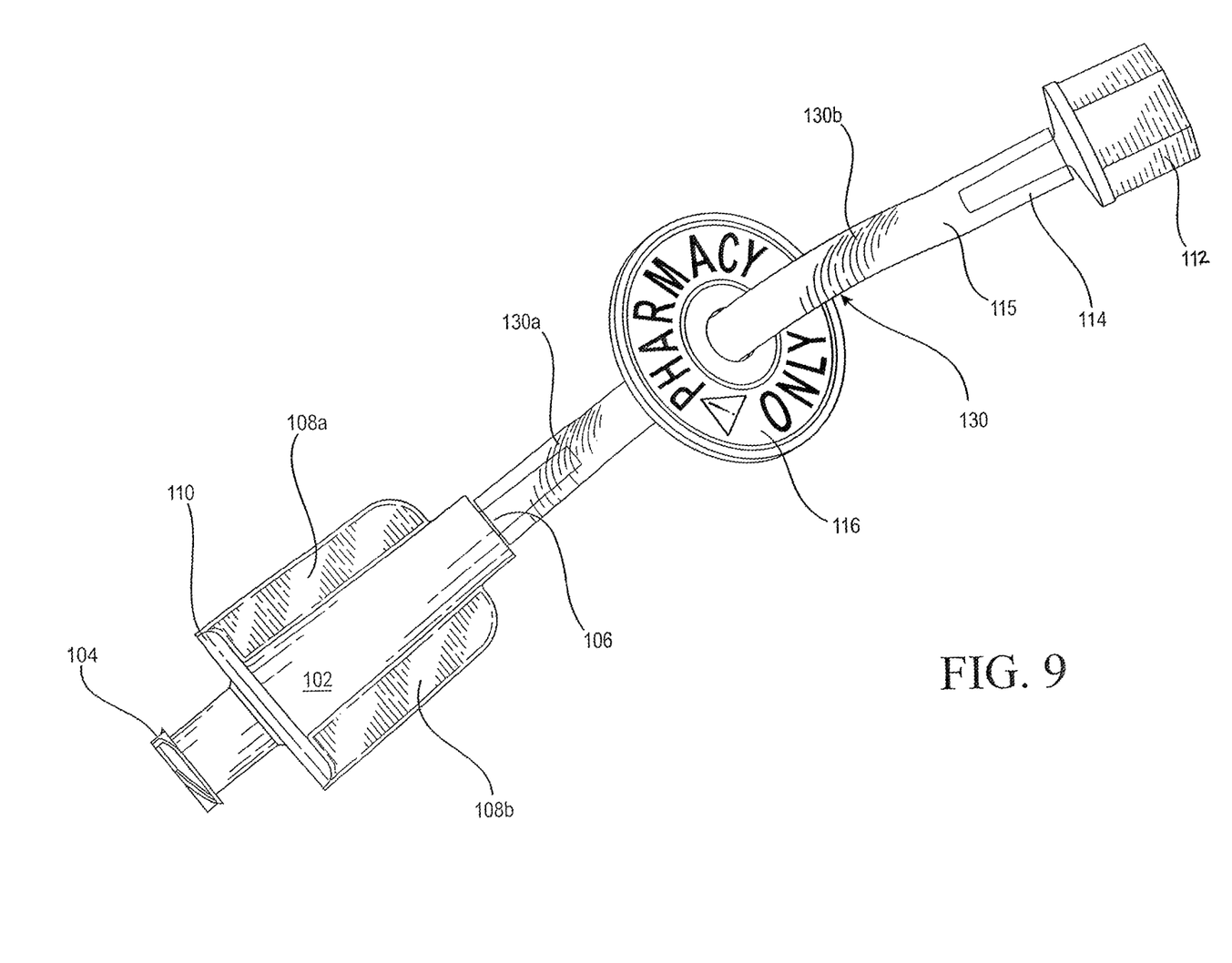
FIG. 9 shows a tubing extended filling fitting of the instant invention.

FIG. 9 is an illustration of an alternate embodiment of the filling fitting of the instant invention. As shown, a flexible tubing 130 interposedly connects the portion of the fitting that has the conventional connector 104 and the portion of the fitting that has the non-conventional connector 112. In particular with reference to the embodiment shown in FIG. 9, tubing 130 has one end 130a fittedly mated to opening 106 of body 102 and another end 130b fittedly mated to opening 115 of extension 114 of non-conventional connector 112. Given that the inside diameter of opening 106 is slightly larger than the outside diameter of extension 114 (since extension 114 is inserted into opening 106 in the embodiment of the fitting as shown in FIGS. 6 and 7), tubing portion 130a has a larger diameter than tubing portion 130b. Portions 130a and 130b of the tubing 130 may be bondedly attached to body 102 and extension 114, respectively, by solvent, as is known in the art. By thus separating and then connecting connectors 104 and 112 by tubing 130, the through passage of the filling fitting of FIG. 9 for fluid path is extended. Being flexible, tubing 130 enables the two end connectors of the extended tube fitting to be matingly coupled to their corresponding counterpart connectors at a position offset from each other. For the FIG. 9 filling fitting, label 116 may be fitted about tubing 130 to convey information to the user.

Alternatively, instead of inserting the respective ends of tubing 130 into corresponding openings at the two portions of the fitting, the respective ends of the tubing may be fitted over the corresponding ends of the two portions of the fitting to make the connection. For example, the end opening of tube portion 130a may be barb fitted about the outer circumferential surface of the extension that forms the opening 106 of body 102 and the end opening of tube portion 130b may be barb fitted about the outer circumferential surface of extension 114. A solvent may be used to bondedly attach the respective ends of the tube to the two portions of the fitting, as discussed above. Note too that the tubing may be formed as an integral part of the extended tube fitting of FIG. 9. When thus moldedly formed as an integral part of the fitting, the tubing of the extended tube fitting would be molded from the same plastic material as the two connector portions of the fitting and thus would not have the same flexibility as the tubing shown in FIG. 9.

To signify that the fitting of the instant invention is adapted to be used as a fitting to fill and/or refill a medicament store such as the cassette of the above-mentioned medicament infusion system, the fitting may be manufactured to have a particular color, for example orange or some other color not commonly associated with fittings or connectors, so that it may be differentiated from other fittings or connectors. If the non-conventional connector and the body of the fitting were manufactured as separate components that are assembled together afterwards, both of those components may be manufactured to have the same color so that after assembly, the resulting filling fitting is color coded throughout.

Although the fitting described hereinabove discloses a conventional female luer connector and a non-conventional male connector, it should be appreciated that there may be instances where a fitting having a conventional male luer connector and a non-conventional female connector may be used to mate to a counterpart conventional female luer connector and a counterpart non-conventional male connector, respectively, in order to establish a fluid path between the devices having the counterpart conventional female luer connector and the counterpart non-conventional male connector.

The invention claimed is:

1. A fitting, comprising:
   a body having a longitudinal portion and a first end and a second end, one through passage in the body connecting the first and second ends, the first end having a conventional luer connector, the second end having an opening to the one through passage;
   a non-conventional connector including an extension adapted to fit into the opening of the body, an other through passage extending along the non-conventional connector and the extension in longitudinal alignment with the one through passage, the non-conventional connector having a given configuration that prevents it from mating with a counterpart conventional luer connector but matable with a counterpart non-conventional connector having a configuration complementary to the given configuration;
   at least one wing extending from and longitudinally along at least a part of a main portion of the body, the wing having a longitudinal top edge; and
   a partition having a surface away from the first end extending circumferentially about the body, the end of the wing facing the first end merging with the surface of the partition with the top edge of the wing align with an outer circumferential edge of the partition.

2. The fitting of claim 1, further comprising:
   a substantially planar member mounted circumferentially about the extension of the non-conventional connector when the extension of the non-conventional connector is non-removably fitted to the opening at the second end of the body;
   wherein the location on the body between the member and the partition defines a position wherein the fingers of a user may grasp the fitting.

3. The fitting of claim 2, wherein the member is adapted to include indicia to convey information to the user, the information may include a message to inform the user that the fitting is to be used only for filling a fluid store from a fluid source.

4. The fitting of claim 1, wherein the extension of the non-conventional connector is integral to the second end of the body so that the fitting is a single one piece fitting with the one and other through passages establishing one continuous through passage connecting the conventional luer connector and the non-conventional connector.

5. The fitting of claim 1, wherein the fitting interposedly connects a fluid source to its first end and a fluid store to its second end to establish a fluid path between the fluid source and the fluid store so that fluid from the fluid source may be transferred to the fluid store to fill the fluid store, the non-conventional connector of the fitting mated to a counterpart non-conventional connector at the fluid store and the conventional luer connector of the fitting mated to a counterpart conventional luer connector at the fluid source to establish the fluid path.

6. The fitting of claim 5, wherein after the fluid store is filled with a desired amount of the fluid and the non-conventional connector of the fitting is disconnected from the counterpart non-conventional connector at the fluid store, the fluid in the fluid store may be infused to a patient when the counterpart non-conventional connector of the fluid store is coupled to a non-conventional connector of the given configuration of a patient infusion device to establish a fluid path between the fluid store and the device, the device infusing the fluid to the patient when it is inserted to the patient.

7. The fitting of claim 1, further comprising a tubing having one end bondedly connected to the opening at the second end of the body and an other end bondedly connected to the extension at the non-conventional connector so that the tubing interposes between the conventional luer connector and the non-conventional connector, the tubing extending the through passage for fluid flow between the first and second ends of the fitting.

8. The fitting of claim 1, wherein there are two wings oppositely extending from and longitudinally along at least a part of the main portion of the body, the wings enabling a user to more readily grasp the fitting.

9. The fitting of claim 1, wherein the fitting has an orange color.

10. A method of manufacturing a fitting adapted to at least establish a fluid path between a fluid store and a fluid source, comprising:
providing a body that includes a longitudinal main portion, a first end and a second end, and one through passage in the body connecting the first and second ends, the second end having an opening;
providing a conventional luer connector at the first end;
providing a non-conventional connector including an extension and an other through passage extending along the non-conventional connector and the extension, the non-conventional connector having a given configuration that prevents it from mating with a counterpart conventional luer connector but matable with a counterpart non-conventional connector having a configuration complementary to the given configuration;
adapting the extension to be fitted into the opening at the second end of the body so that the one and other through passages are in longitudinal alignment with each other to establish one continuous through passage;
extending at least one wing having a top edge from and longitudinally along at least a part of the body; and
extending a partition having a surface away from the first end circumferentially about the body, the end of the wing facing the first end merging with the surface of the partition with the top edge of the wing aligned with an outer circumferential edge of the partition.

11. The method of claim 10, further comprising:
mounting a substantially planar member circumferentially about the extension of the non-conventional connector when the extension of the non-conventional connector is fitted into the opening at the second end of the body so that the member non-removably extends circumferentially about the extension;
wherein the planar member and the partition define therebetween a location on the body whereat the fingers of a user may be positioned to grasp the fitting.

12. The method of claim 11, further comprising providing indicia on the member to convey information to a user of the fitting.

13. The method of claim 10, wherein the extension of the non-conventional connector and the second end of the body are integrally formed so that the fitting is a single one piece integral fitting.

14. The method of claim 10, further comprising:
coloring the fitting to have an orange color.

15. The method of claim 10, further comprising:
extending two wings oppositely from and longitudinally along at least a part of the main portion of the body to assist a user in grasping the fitting.

16. The method of claim 10, wherein the fitting manufactured is used by:
mating the conventional luer connector at the first end of the fitting to a counterpart conventional luer connector of a fluid source; and
mating the non-conventional connector of the fitting to a counterpart non-conventional connector of a fluid store to establish a fluid path between the fluid source and the fluid store so that fluid may flow between the fluid source and the fluid store, and the fluid store may be filled with fluid from the fluid source.

17. The method of claim 16, further comprising:
disconnecting the non-conventional connector of the fitting from the counterpart non-conventional connector at the fluid store after the fluid store is filled with a desired amount of the fluid; and
coupling the counterpart non-conventional connector of the fluid store to a non-conventional connector of the given configuration of a patient infusion device to establish a fluid path between the fluid store and the device;
wherein the device may be inserted to the patient so that the fluid in the fluid store may be infused to a patient.

18. The method of claim 10, further comprising:
interposing a tubing between the conventional luer and non-conventional connectors;
bondedly connecting one end of the tubing to the opening at the second end of the body; and
bondedly connecting an other end of the tubing to the extension at the non-conventional connector;
wherein the tubing extends the through passage for fluid flow between the first and second ends of the fitting.

19. A fitting, comprising:
a body having a longitudinal portion including a first end and a second end, one through passage in the body connecting the first and second ends, the first end having a luer connector, the second end having an opening to the one passage;

a connector including an extension fitted to the opening, an other through passage extending along the connector and the extension, the connector having a given configuration that prevents it from mating with any luer connector but matable with a counterpart connector having a configuration complementary to the given configuration;

at least one wing having a longitudinal top edge extending from and longitudinally along at least a portion of the body; and a partition having a surface away from the first end extending circumferentially about the body proximate to one of the first and second ends to merge with one end of the wing so that the top edge of the wing comes into alignment with an outer circumferential edge of the partition.

20. The fitting of claim 19, further comprising:

a substantially planar member mounted circumferentially about the extension away from the partition.

* * * * *